(12) United States Patent
Golz et al.

(10) Patent No.: US 7,833,749 B2
(45) Date of Patent: Nov. 16, 2010

(54) ISOLATED PHOTOPROTEIN MTCLYTIN, AND USE THEREOF

(75) Inventors: Stefan Golz, Essen (DE); Svetlana Markova, Krasnoyarsk (RU); Ludmila Burakova, Sosnovoborsk (RU); Ludmila Frank, Krasnoyarsk (RU); Eugene Vysotski, Krasnoyarsk (RU)

(73) Assignee: Axxam S.p.A. (IT)

( * ) Notice: Subject to any disclaimer, the term of this patent is extended or adjusted under 35 U.S.C. 154(b) by 720 days.

(21) Appl. No.: 10/572,175

(22) PCT Filed: Sep. 3, 2004

(86) PCT No.: PCT/EP2004/009843

§ 371 (c)(1), (2), (4) Date: May 16, 2007

(87) PCT Pub. No.: WO2005/035559

PCT Pub. Date: Apr. 21, 2005

(65) Prior Publication Data

US 2007/0275377 A1    Nov. 29, 2007

(30) Foreign Application Priority Data

Sep. 16, 2003 (DE) .................................. 103 42 670

(51) Int. Cl.
*C12P 21/06* (2006.01)
*C07H 17/00* (2006.01)
*C07K 14/00* (2006.01)

(52) U.S. Cl. .................. 435/69.1; 435/320.1; 536/23.1; 530/300

(58) Field of Classification Search ....................... None
See application file for complete search history.

(56) References Cited

U.S. PATENT DOCUMENTS 5,648,218 A * 7/1997 Stults ............................ 435/6
7,601,805 B2 * 10/2009 Foti et al. .................... 530/350

FOREIGN PATENT DOCUMENTS

WO    WO 91/01305 A1    2/1991
WO    WO 03/006497 A2    1/2003

OTHER PUBLICATIONS

Dunstan, S. L., et al., "Cloning and Expression of the Bioluminescent Photoprotein Pholasin from the Bivalve Mullusc *Pholas dactylus*", J. Biol. Chem., 275(13): 9403-9409 (Mar. 2000).
Database UniProt, Oct. 1, 1994, Inouye, S., et al., "Clytin Precursor (Phialidin)", Database Accession No. Q08121, XP002300448.
Inouye, S., et al., "Cloning and sequence analysis of cDNA for the $Ca^{2+}$-activated photoprotein, clytin", FEBS Letters, 315(3): 343-346 (Jan. 1993).
Database Embl Mar. 10, 2002, Markova, S. V., et al., "*Obelia geniculata* apoobelin mRNA, complete cds", Database Accession No. AF394688, XP002305433.
Markova, S. V., et al., "Obelin from the Bioluminiscent Marine Hydroid *Obelia geniculata*: Cloning, Expression, and Comparison of Some Properties with Those of Other $Ca^{2+}$-Regulated Photoproteins", Biochem., 41: 2227-2236 (2002).

* cited by examiner

*Primary Examiner*—Karen Cochrane Carlson
(74) *Attorney, Agent, or Firm*—Edwards Angell Palmer & Dodge LLP; Ralph A. Loren; Amy DeCloux

(57) ABSTRACT

The invention relates to the photoprotein mtClytin, to its nucleotide and amino acid sequences and to the activity and use of the photoprotein mtClytin.

12 Claims, 9 Drawing Sheets

Fig. 7

```
         1                                                50
Clytin   ..........  ..........  ..........  ..........  ..........
mtClytin GACAGATAAA  AAATTCACTC  CTTAGATTAT  TTAGTGAATA  AGAGAAAAAA 51                                               100
Clytin   ..........  ..........  ..........  ..........  ..........
mtClytin AGGATAAGAA  ATCAAGATGC  AAAGGTTTAC  AAATCGTCTT  CTTTCCATGT 101                                              150
Clytin   ..........  ......ATCA  ACTTTTGCAA  CTCAAAGCAA  ATTTCAAAAC
mtClytin CGGCTTTACG  TGCAAGATCA  AGATT.GCAA  CGCACGGCAA  ATTTTCACAC 151                                              200
Clytin   TTCAACATGG  CTGAC.ACTG  CATCAAAATA  CGCCGTCAAA  CTCAGACCCA
mtClytin CAGCATACTC  TTGGCTACAG  ATTCAAAATA  CGCGGTCAAA  CTCGATCCTG 201                                              250
Clytin   ACTTCGACAA  CCCAAAATGG  GTCAACAGAC  ACAAATTTAT  GTTCAACTTT
mtClytin ATTTTGCAAA  TCCAAAATGG  ATCAACAGAC  ACAAATTTAT  GTTCAACTTT 251                                              300
Clytin   TTGGACATTA  ACGGCGACGG  AAAAATCACT  TTGGATGAAA  TCGTCTCCAA
mtClytin TTGGACATAA  ACGGTAAGGG  GAAAATCACA  TTAGATGAAA  TCGTCTCCAA 301                                              350
Clytin   AGCTTCGGAT  GACATTTGCG  CCAAACTTGG  AGCAACACCA  GAACAGACCA
mtClytin AGCTTCAGAC  GACATTTGTG  CTAAACTGGA  TGCAACACCA  GAACAGACCA 351                                              400
Clytin   AACGTCACCA  GGATGCTGTC  GAAGCTTTCT  TCAAAAAGAT  TGGTATGGAT
mtClytin AACGTCACCA  GGATGCTGTT  GAAGCCTTTT  TCAAGAAAAT  GGGCATGGAT 401                                              450
Clytin   TATGGTAAAG  AAGTCGAATT  CCCAGCTTTT  GTTGATGGAT  GGAAAGAACT
mtClytin TATGGTAAAG  AAGTTGCATT  CCCAGAATTT  ATTAAGGGAT  GGGAAGAGTT 451                                              500
Clytin   GGCCAATTAT  GACTTGAAAC  TTTGGTCTCA  AAACAAGAAA  TCTTTGATCC
mtClytin GGCCGAACAC  GACTTGGAAC  TCTGGTCTCA  AAACAAAAGT  ACATTGATCC 501                                              550
Clytin   GCGACTGGGG  AGAAGCTGTT  TTCGACATTT  TTGACAAAGA  CGGAAGTGGC
mtClytin GTGAATGGGG  AGATGCTGTT  TTCGACATTT  TCGACAAAGA  CGCAAGTGGC
```

Fig. 7 continued

```
          551                                                        600
Clytin    TCAATCAGTT TGGACGAATG GAAGGCTTAT GGACGAATCT CTGGAATCTG
mtClytin  TCAATCAGTT TAGACGAATG GAAGGCTTAC GGACGAATCT CTGGAATCTG 601                                                        650
Clytin    CTCATCAGAC GAAGACGCCG AAAAGACCTT CAAACATTGC GATTTGGACA
mtClytin  TCCATCAGAC GAAGACGCTG AGAAGACGTT CAAACATTGT GATTTGGACA 651                                                        700
Clytin    ACAGTGGCAA ACTTGATGTT GATGAGATGA CCAGACAACA TTTGGGATTC
mtClytin  ACAGTGGCAA ACTTGATGTT GATGAGATGA CCAGGCAACA TTTAGGCTTC 701                                                        750
Clytin    TGGTACACCT TGGACCCCAA CGCTGATGGT CTTTACGGCA ATTTTGTTCC
mtClytin  TGGTACACAT TGGATCCAAC TTCTGATGGT CTTTATGGCA ATTTTGTTCC 751                                                        800
Clytin    TTAAACATCG ...AAACAAA AGCCCAAAAG AAGTTTTGGA AGAATTATTT
mtClytin  CTAAGAAGCG TTCAGTTAAA AACGCTAAAC ATTGTTCAGT TGTAAAATTA 801                                                        850
Clytin    GATAC..TAT CATTTG.... ..TTACTATT TCGTAACATG CT..ATATTT
mtClytin  TATTCATTTT CATTTCGTAA AATTAGTATT TATAAATTTG TATCATAAAT 851                                                        900
Clytin    TGTAAC.ATG CTATATT.TA AATAATTTT. .......... ..........
mtClytin  TGTATCCATG TTGTAGACTA AATAAGACTC GGCAAAAAAA AAAAAAAAA 901        913
Clytin    .......... ...
mtClytin  AAAAAAAAAA AAA
```

Fig. 8

```
                1                                                    50
mtClytin    MQRFTNRLLS MSALRARSRL QRTANFHTSI LLATDSKYAV KLDPDFANPK
Clytin      .......... .......... .......... MADTASKYAV KLRPNFDNPK 51                                                   100
mtCyltin    WINRHKFMFN FLDINGKGKI TLDEIVSKAS DDICAKLDAT PEQTKRHQDA
Clytin      WVNRHKFMFN FLDINGDGKI TLDEIVSKAS DDICAKLGAT PEQTKRHQDA 101                                                  150
Clytin      VEAFFKKMGM DYGKEVAFPE FIKGWEELAE HDLELWSQNK STLIREWGDA
Clytin      VEAFFKKIGM DYGKEVEFPA FVDGWKELAN YDLKLWSQNK KSLIRDWGEA 151                                                  200
Clytin      VFDIFDKDAS GSISLDEWKA YGRISGICPS DEDAEKTFKH CDLDNSGKLD
Clytin      VFDIFDKDGS GSISLDEWKA YGRISGICSS DEDAEKTFKH CDLDNSGKLD 201                        228
mtClytin    VDEMTRQHLG FWYTLDPTSD GLYGNFVP
Clytin      VDEMTRQHLG FWYTLDPNAD GLYGNFVP
```

Fig. 9

```
1                                                                    50
mtClytin    MQRFTNRLLS MSALRARSRL QRTANFHTSI LLATDSKYAV KLDPDFANPK
clytin-2    .......... .......... .......... MTDTASKYAV KLKTNFEDPK
  Clytin    .......... .......... .......... MADTASKYAV KLRPNFDNPK 51                                                   100
mtClytin    WINRHKFMFN FLDINGKGKI TLDEIVSKAS DDICAKLDAT PEQTKRHQDA
clytin-2    WVNRHKFMFN FLDINGNGKI TLDEIVSKAS DDICAKLGAT PAQTQRHQEA
  Clytin    WVNRHKFMFN FLDINGDGKI TLDEIVSKAS DDICAKLGAT PEQTKRHQDA 101                                                  150
mtClytin    VEAFFKKMGM DYGKEVAFPE FIKGWEELAE HDLELWSQNK STLIREWGDA
clytin-2    VEAFFKKIGL DYGKEVEFPA FVNGWKELAK HDLKLWSQNK KSLIRNWGEA
  Clytin    VEAFFKKIGM DYGKEVEFPA FVDGWKELAN YDLKLWSQNK KSLIRDWGEA 151                                                  200
mtClytin    VFDIFDKDAS GSISLDEWKA YGRISGICPS DEDAEKTFKH CDLDNSGKLD
clytin-2    VFDIFDKDGS GSISLDEWKT YGGISGICPS DEDAEKTFKH CDLDNSGKLD
  Clytin    VFDIFDKDGS GSISLDEWKA YGRISGICSS DEDAEKTFKH CDLDNSGKLD 201                        228
mtClytin    VDEMTRQHLG FWYTLDPTSD GLYGNFVP
clytin-2    VDEMTRQHLG FWYTLDPNAD GLYGNFVP
  Clytin    VDEMTRQHLG FWYTLDPNAD GLYGNFVP
```

ISOLATED PHOTOPROTEIN MTCLYTIN, AND USE THEREOF

This application is a 371 of PCT/EP2004/009843, filed Sep. 3, 2004.

The invention relates to the photoprotein mtClytin, to its nucleotide and amino acid sequences and to the activity and use of the photoprotein mtClytin.

Photoproteins

The phenomenon of the generation of light by living organisms is designated bioluminescence. It is the result of biochemical reactions in cells, in which reactions the chemical energy is emitted in the form of light quanta (what is termed cold emission by means of chemoluminescence). While the light which is produced in this way is monochromatic, since it is emitted in connection with a discrete electron transfer, it can be shifted by secondary luminescent dyes (e.g. fluorescent proteins in the case of luminescent jellyfish of the genus *Aequoria*) into spectral regions of longer wavelength.

Bioluminescence has a diversity of biological functions: at an ocean depth of between 200 and 1000 m (mesopelagial), about 90% of all living organisms luminesce. In this case, the luminescent signals are employed for attracting partners, for deception and as a lure. Glowworms and fireflies also use the light signals for seeking partners. On the other hand, the significance of the luminescence of bacteria, fungi and single-cell algae is unclear. It is assumed that it is used for coordinating many single individuals in a large population or else represents a type of biological clock.

A large number of coelenterates are bioluminescent (Morin et al., 1974). These organisms emit blue or green light. As an isolated protein, aequorin, which is derived from *Aequoria victoria* (Shimomura et al., 1969) and which, in 1962, was the first light-producing protein to be identified, emitted a blue light, and not a green light as observed phenotypically in the case of *Aequoria victoria*. The green fluorescent protein (GFP) which, as a result of being activated by aequorin, causes *Aequoria victoria* to appear phenotypically green was subsequently isolated from this medusa (Johnson et al., 1962; Hastings et al., 1969; Inouye et al., 1994). Other photoproteins which have also been identified and described are clytin (Inouye et al., 1993), mitrocomin (Fagan et al., 1993) and obelin (Illarionov et al., 1995).

TABLE 1

Overview of some photoproteins. The table gives the name, the organism from which the protein has been isolated and the identification number (Acc. No.) of the database entry.

| Name | Organism | Identification No. |
| --- | --- | --- |
| Obelin | *Obelia geniculata* | AAL86372 |
| Clytin | *Clytia gregaria* | CAA49754 |
| Aequorin | *Aequorea macrodactyla* | AAK02061 |
| Aequorin | *Aequorea parva* | AAK02060 |
| Mitrocomin | *Mitrocoma cellularia* | AAA29298 |
| Pholasin | *Pholas dactylus* | AAM18085 |
| ? | *Symplectoteuthis oualaniensis* | AX305029 |

TABLE 2

Overview of some photoproteins. The table gives the organism from which the protein has been isolated, the name of the photoprotein and a selection of patents or applications.

| Organism | Fluorescent protein | Patent/Application |
| --- | --- | --- |
| *Obelia geniculata* | Obelin | WO03006497 |
| *Clytia gregaria* | Clytin | WO03006497 |
| *Aequoria victoria* | Aequorin | WO200168824 |
| | | US-0908909 |
| | | US 6,152,358 |
| | | JP-0176125 |
| *Pholas dactylus* | Pholasin | WO0028025 |
| | | GB-0024357 |

Bioluminescence is nowadays used in technology in a wide variety of ways, e.g. in the form of bioindicators of environmental pollution or in biochemistry for sensitively detecting proteins or for quantifying particular compounds, or as what are termed reporters in connection with investigating gene regulation in the cell.

The photoproteins differ not only in their nucleotide and amino acid sequences but also in their biochemical and physical properties.

It has been demonstrated that the physical and biochemical properties of photoproteins can be altered by altering the amino acid sequences of these proteins. Examples of mutagenized photoproteins are described in the literature (U.S. Pat. No. 6,495,355; U.S. Pat. No. 5,541,309; U.S. Pat. No. 5,093,240; Shimomura et al., 1986).

The abovementioned photoproteins generate light by oxidizing coelenterazine (Haddock et al., 2001; Jones et al., 1999).

Reporter Systems

In general, genes whose gene products can be readily detected using simple biochemical or histochemical methods are termed reporter genes or indicator genes. At least 2 types of reporter gene are distinguished.

1. Resistance genes. This is the term used for genes whose expression confers, on a cell, resistance to antibiotics or other substances whose presence in the growth medium leads to the death of the cell if the resistance gene is absent.
2. Reporter genes. The products of reporter genes are used in genetic manipulation as fused or unfused indicators. The commonest reporter genes include beta-galactosidase (Alam et al., 1990), alkaline phosphatase (Yang et al., 1997; Cullen et al., 1992), and luciferases and other photoproteins (Shinomura, 1985; Phillips G N, 1997; Snowdowne et al., 1984).

The emission of photons in the visible spectral range, with this emission being effected by means of excited emitter molecules, is termed luminescence. In contrast to fluorescence, the energy is not, in this case, supplied from the exterior in the form of radiation of shorter wavelength.

A distinction is made between chemoluminescence and bioluminescence. A chemical reaction which leads to an excited molecule which itself luminesces when the excited electrons return to the basal state is termed chemoluminescence. If this reaction is catalyzed by an enzyme, the phenomenon is then referred to as being bioluminescence. The enzymes involved in the reaction are generally termed luciferases.

Classification of the Species *Clytia gregaria*

Cnidaria→Leptomedusae→Campanulariidae→*Clytia gregaria*

The species *Clytia gregaria* belongs to the Cnidaria, specifically to the Medusae. The bioluminescent and fluorescent phenotype, respectively, has already been described in 1998 (Ward Isolating the cDNA In order to investigate the bioluminescence activity of the species *Clytia gregaria*, specimens were caught in the White Sea (Kartesh Biological Station, Russia) and stored in liquid nitrogen. In order to construct the *Clytia gregaria* cDNA libraries, the poly(a)+ RNA was isolated using the "Straight A" isolation method from Novagen (USA).

An RT-PCR was carried out for preparing the cDNA. For this, 1 µg of RNA was incubated with reverse transcriptase (Superscript Gold II) in accordance with the following scheme:

| PCR | 1. | 30 seconds | 95° C. |
|---|---|---|---|
|  | 2. | 6 minutes | 68° C. |
|  | 3. | 10 seconds | 95° C. |
|  | 4. | 6 minutes | 68° C. |
| 17 cycles of step 4 after step 3 | | | |

The reaction products were incubated with proteinase K, at 37° C. for 30 minutes, in order to inactivate the polymerase, and the cDNA was precipitated with ethanol. The cDNA expression library was constructed using the Clontech (USA) "SMART cDNA" library construction kit in accordance with the manufacturer's instruction. The cDNA was cloned into the expression vector pTrip1Ex2 (Clontech; USA). The expression vectors were transformed by electroporation into bacteria of the strain *E. coli* XL1 blue.

The bacteria were plated out on solid LB nutrient medium and incubated at 37° C. for 24 hours. A replica plating was then carried out, with the bacteria being transferred to another solid nutrient medium plate using a nitrocellulose filter. The replica plate was in turn incubated at 37° C. for 24 hours and the bacterial colonies which had grown were transferred into liquid LB medium. After IPTG (final concentration, 0.1 mM) had been added, the bacteria were incubated at 37° C. for 4 hours on a shaker. The bacteria were harvested by centrifugation and the bacterial mass was resuspended, at 0° C., in 0.5 ml of disruption buffer (5 mM EDTA, 20 mM Tris-HCL, pH 9.0). The bacteria were then disrupted by ultrasonication.

After adding coelenterazine (final concentration, 10E-07 M), the lysates were incubated at 4° C. for 3 hours. The bioluminescence was then measured in a luminometer after adding calcium chloride (final concentration, 20 mM).

A photoprotein was identified. The photoprotein was designated mtClytin. The photoprotein mtClytin is described in detail below.

mtClytin

With an identity of 87%, the photoprotein mtClytin exhibits the highest homology at the amino acid level with clytin from *Clytia gregaria* and an identity of 77% with obelin from *Obelia geniculata* (shown in Example 8; FIG. 8). The homology of 87%—in relation to clytin—occurs at the C-terminal end of the protein, multiple amino acid substitutions being identifiable distributed over the entire protein. At the nucleic acid level, the identity is less than 30% (shown in Example 7; FIG. 7). The BLAST method (Altschul et al., 1997) was used for the sequence comparison.

The photoprotein clytin-2 exhibits the highest homology at the amino acid level with clytin from *Clytia gregaria*. However, the sequence exhibits a number of differences in the amino acid sequence, with these differences being depicted in Example 11 (FIG. 9). These differences can lead to changes in physicochemical, biochemical and bioluminescent properties. The photoprotein clytin-2 does not possess any signal peptide (as shown in Example 10).

The photoprotein mtClytin possesses a signal peptide which can lead to the photoprotein being translocated into mitochondria. The signal peptide was identified by the computer program MITOPROT (Claros et al., 1996) (shown in Example 10). The signal peptide which was determined by MITOPROT is given in SEQ ID NO: 3. The photoprotein mtClytin is the first photoprotein in which a natural signal peptide for translocation into mitochondria has been identified.

The invention also relates to functional equivalents of mtClytin. Functional equivalents are those proteins which have comparable physicochemical properties and are at least 70% homologous with SEQ ID NO: 2. Preference is given to a homology of at least 80% or 90%. A homology of at least 95% is particularly preferred.

The invention also relates to the functional equivalents of the mtclytin signal peptide. Functional equivalents are those proteins or peptides which have comparable physicochemical properties and are at least 70% homologous to SEQ ID NO: 3. Preference is given to a homology of at least 80% or 90%. A homology of at least 95% is particularly preferred.

The photoprotein mtClytin is suitable for being used as a reporter gene for cellular systems, especially for receptors, for ion channels, for transporters, for transcription factors or for inducible systems.

The mtClytin signal peptide is also suitable for being fused to reporter genes in order to be used as a fused reporter gene for cellular systems, especially for receptors, for ion channels, for transporters, for transcription factors or for inducible systems.

The photoprotein mtClytin is also suitable for being used as a reporter gene by labeling, identifying and characterizing cell organelles, especially for mitochondria.

The mtClytin signal peptide is also suitable for being fused to peptides or proteins for translocation into cell organelles, especially mitochondria.

The photoprotein mtClytin is also suitable for being used as a reporter gene for determining parameters inside and outside cell organelles, especially mitochondria, especially calcium concentrations.

The mtClytin signal peptide is also suitable, as a fusion peptide, for being used as a reporter gene for determining parameters inside and outside cell organelles, especially mitochondria, especially calcium concentrations.

The photoprotein mtClytin is suitable for being used as a reporter gene in bacterial and eukaryotic systems, especially in mammalian cells, in bacteria, in yeasts, in baculo and in plants.

The photoprotein mtClytin is suitable for being used as a reporter gene for cellular systems in combination with bioluminescent or chemoluminescent systems, especially systems using luciferases, using oxygenases or using phosphatases.

The mtClytin signal peptide is also suitable, as fusion peptide, for being used as a reporter gene for cellular systems in combination with bioluminescent or chemoluminescent systems, especially systems using luciferases, using oxygenases or using phosphatases.

The photoprotein mtClytin is suitable for being used as a fusion protein, especially for receptors, for ion channels, for transporters, for transcription factors, for proteinases, for kinases, for phosphodiesterases, for hydrolases, for peptidases, for transferases, for membrane proteins and for glycoproteins.

The mtClytin signal peptide is also suitable, as fusion peptide, for being used as a fusion protein, especially for receptors, for ion channels, for transporters, for transcription factors, for proteinases, for kinases, for phosphodiesterases, for hydrolases, for peptidases, for transferases, for membrane proteins and for glycoproteins.

The photoprotein mtClytin is suitable for being immobilized, especially by antibodies, by biotin, or by magnetic or magnetizable supports.

The photoprotein mtClytin is suitable for being used as a protein for energy transfer systems, especially FRET (fluorescence resonance energy transfer), BRET (bioluminescence resonance energy transfer), FET (field effect transistors), FP (fluorescence polarization) and HTRF (homogeneous time-resolved fluorescence) systems.

The photoprotein mtClytin is suitable for labeling substrates or ligands, especially for proteases, for kinases or for transferases.

The photoprotein mtClytin is suitable for being expressed in bacterial systems, especially for titer determination, as a substrate for biochemical systems, especially for proteinases and kinases.

The photoprotein mtClytin is suitable for being used as a label, especially coupled to antibiotics, coupled to enzymes, coupled to receptors or coupled to ion channels and other proteins.

The mtClytin signal peptide is also suitable, as fusion peptide, for being used as a label, especially coupled to antibiotics, coupled to enzymes, coupled to receptors or coupled to ion channels and other proteins.

The photoprotein mtClytin is suitable for being used as a reporter gene in the search for pharmacological active compounds, especially in HTS (high throughput screening).

The mtClytin signal peptide is also suitable for being used as a reporter gene in the search for pharmacological active compounds, especially in HTS (high throughput screening).

The photoprotein mtClytin is suitable for being used as a component of detection systems, especially for ELISA (enzyme-linked immunosorbent assay), for immunohistochemistry, for Western blotting or for confocal microscopy.

The photoprotein mtClytin is suitable for being used as a label for analyzing interactions, especially for protein-protein interactions, for DNA-protein interactions, for DNA-RNA interactions, for RNA-RNA interactions, or for RNA-protein interactions (DNA: desoxyribonucleic acid; RNA: ribonucleic acid).

The photoprotein mtClytin is suitable for being used as a label or fusion protein for expression in transgenic organisms, especially in mice, in rats, in hamsters and other mammals, in primates, in fish, in worms or in plants.

The mtClytin signal peptide is also suitable, as fusion peptide, for being used as a label or fusion protein for expression in transgenic organisms, especially in mice, in rats, in hamsters and other mammals, in primates, in fish, in worms or in plants.

The photoprotein mtClytin is suitable for being used as a label or fusion protein for analyzing embryonic development.

The photoprotein mtClytin is suitable for being used as a label by way of a coupling mediator, especially by way of biotin, by way of NHS (N-hydroxysulfosuccimide) or by way of CN—Br.

The photoprotein mtClytin is suitable for being used as a reporter which is coupled to nucleic acids, especially to DNA or RNA.

The photoprotein mtClytin is suitable for being used as a reporter which is coupled to proteins or peptides.

The mtClytin signal peptide is also suitable, as fusion peptide, for being used as a reporter which is coupled to proteins or peptides.

The photoprotein mtClytin is suitable for being used as a reporter for measuring intracellular or extracellular calcium concentrations.

The photoprotein mtClytin is suitable for characterizing signal cascades in cellular systems.

The photoprotein mtClytin which is coupled to nucleic acids or peptides is suitable for being used as a probe, especially for Northern blots, for Southern blots, for Western blots, for ELISA, for nucleic acid sequencings, for protein analyses or for chip analyses.

The photoprotein mtClytin is suitable for being used for labeling pharmacological formulations, especially infectious agents, antibodies or "small molecules".

The photoprotein mtClytin is suitable for being used for geological investigations, especially for ocean, groundwater and river currents.

The photoprotein mtClytin is suitable for being expressed in expression systems, especially in in-vitro translation systems, in bacterial systems, in yeast systems, in baculo systems, in viral systems and in eukaryotic systems.

The mtClytin signal peptide is also suitable, as fusion peptide, for being expressed in expression systems, especially in in-vitro translation systems, in bacterial systems, in yeast systems, in baculo systems, in viral systems and in eukaryotic systems.

The photoprotein mtClytin is suitable for visualizing tissues or cells in connection with surgical interventions, especially in connection with invasive, in connection with noninvasive and in connection with minimally invasive interventions.

The photoprotein mtClytin is also suitable for labeling tumor tissues and other phenotypically altered tissues, especially in connection with histological investigation and in connection with surgical interventions.

The invention also relates to the purification of the photoprotein mtClytin, especially as a wild-type protein, as a fusion protein and as a mutagenized protein.

The invention also relates to the purification of the mtClytin signal peptide, especially as a wild-type protein, as a fusion protein and as a mutagenized protein.

The invention also relates to the use of the photoprotein mtClytin in the field of cosmetics, especially bath additives, lotions, soaps, body dyes, toothpaste and body powders.

The invention also relates to the use of the photoprotein mtClytin for dyeing, especially dyeing foodstuffs, bath additives, ink, textiles and plastics.

The invention also relates to the use of the photoprotein mtClytin for dyeing paper, especially greetings cards, paper products, wallpapers and handicraft articles.

The invention also relates to the use of the photoprotein mtClytin for dyeing liquids, especially for water pistols, fountains, beverages and ice.

The invention also relates to the use of the photoprotein mtClytin for producing toys, especially finger dye and makeup.

The invention relates to nucleic acid molecules which encode the polypeptide which is disclosed by SEQ ID NO: 2.

The invention relates to nucleic acid molecules which encode the polypeptide which is disclosed by SEQ ID NO: 3.

The invention relates to nucleic acid molecules which encode the polypeptide which is disclosed by SEQ ID NO: 6.

The invention relates to the polypeptide having the amino acid sequence which is disclosed in SEQ ID NO: 2.

The invention relates to the polypeptide having the amino acid sequence which is disclosed in SEQ ID NO: 3.

The invention relates to the polypeptide having the amino acid sequence which is disclosed in SEQ ID NO: 6.

The invention furthermore relates to nucleic acid molecules which are selected from the group consisting of
  a) nucleic acid molecules which encode a polypeptide which contains the amino acid sequence disclosed by SEQ ID NO: 2;
  b) nucleic acid molecules which contain the sequence depicted by SEQ ID NO: 1;
  c) nucleic acid molecules whose complementary strand hybridizes with a nucleic acid molecule from a) or b) under stringent conditions and which encode a polypeptide which exhibits the biological function of a photoprotein;
    A stringent hybridization of nucleic acid molecules can be carried out, for example, in an aqueous solution comprising 0.2×SSC (1× standard saline citrate=150 mM NaCl, 15 mM trisodium citrate) at 68° C. (Sambrook et al., 1989).
  d) nucleic acid molecules which differ from the nucleic acid molecules mentioned under c) due to the degeneracy of the genetic code;
  e) nucleic acid molecules which exhibit a sequence homology with SEQ ID NO: 1 of at least 95% and whose protein product exhibits the biological function of a photoprotein; and
  f) nucleic acid molecules which exhibit a sequence homology with SEQ ID NO: 1 of at least 65% and whose protein product exhibits the biological function of a photoprotein.

The invention also relates to nucleic acid molecules which exhibit a sequence homology with SEQ ID NO: 1 or SEQ ID NO: 5 of at least 95%, 90%, 85%, 80%, 75%, 70%, 65% or 60% and which encode a polypeptide which possesses the properties of a photoprotein.

The invention also relates to nucleic acid molecules which exhibit a sequence homology with SEQ ID NO: 4 of at least 95%, 90%, 85%, 80%, 75%, 70%, 65% or 60% and which encode a polypeptide which possesses the properties of a signal or leader peptide.

The invention relates to the abovementioned nucleic acid molecules in which the sequence contains a functional promoter 5' to the photoprotein-encoding sequence or to the leader- or signal-sequence-encoding sequence.

The invention also relates to nucleic acid molecules as previously described which are constituents of recombinant DNA or RNA vectors.

The invention relates to organisms which harbor such a vector.

The invention relates to oligonucleotides having more than 10 consecutive nucleotides which are identical or complementary to the DNA or RNA sequence of the mtClytin molecules or of the other molecules according to the invention.

The invention relates to photoproteins which are encoded by the previously described nucleotide sequences.

The invention relates to methods for expressing the photoprotein polypeptides according to the invention in bacteria, in eukaryotic cells or in in-vitro expression systems.

The invention also relates to methods for purifying/isolating a photoprotein polypeptide according to the invention.

The invention relates to peptides which have more than 5 consecutive amino acids and which are immunologically recognized by antibodies directed against the photoproteins according to the invention.

The invention relates to the use of the photoprotein-encoding nucleic acids according to the invention as marker genes or reporter genes, in particular for searching for pharmacological active compounds and for diagnostics.

The invention relates to the use of the photoproteins according to the invention or of a photoprotein-encoding nucleic acid according to the invention as labels or reporters or as a marker gene or reporter gene.

The invention relates to the use of the photoprotein mtClytin (SEQ ID NO: 2), or to the use of a nucleic acid which encodes the photoprotein mtClytin as a label or reporter, or as a label or reporter gene, in particular for searching for pharmacological active compounds and for diagnostics.

The invention relates to the use of the nucleic acid depicted in SEQ ID NO: 1 as a marker gene or reporter gene, in particular for searching for pharmacological active compounds and diagnostics.

The invention relates to the use of the peptide depicted in SEQ ID NO: 6 and its underlying nucleic acid sequence SEQ ID NO: 5 as a marker gene or reporter gene, in particular for searching for pharmacological active compounds and diagnostics.

The invention also relates to polyclonal or monoclonal antibodies which recognize a polypeptide according to the invention.

The invention also relates to monoclonal or polyclonal antibodies which recognize the photoprotein mtClytin (SEQ ID NO: 2) or the photoprotein clytin-2 (SEQ ID NO: 6).

The invention also relates to monoclonal or polyclonal antibodies which recognize the signal peptide of the photoprotein mtClytin (SEQ ID NO: 3).

The invention furthermore relates to a nucleic acid molecule which is selected from the group consisting of
  a) nucleic acid molecules which encode a polypeptide which contains the amino acid sequence disclosed by SEQ ID NO: 3;
  b) nucleic acid molecules which contain the sequence depicted by SEQ ID NO: 4;
  c) nucleic acid molecules whose complementary strand hybridizes with a nucleic acid molecule from a) or b) under stringent conditions and which encode a peptide which exhibits the biological function of a signal or leader peptide;
  d) nucleic acid molecules which differ from the nucleic acid molecules mentioned under c) due to the degeneracy of the genetic code;
  e) nucleic acid molecules which exhibit a sequence homology with SEQ ID NO: 4 of at least 95% and encode a peptide which has the biological function of a signal or leader peptide; and
  f) nucleic acid molecules which exhibit a sequence homology with SEQ ID NO: 4 of at least 65% and encode a peptide which has the biological function of a signal or leader peptide.

The invention likewise relates to a nucleic acid molecule which is selected from the group consisting of
  a) nucleic acid molecules which encode a polypeptide which contains the amino acid sequence disclosed by SEQ ID NO: 6;
  b) nucleic acid molecules which contain the sequence depicted by SEQ ID NO: 5;
  c) nucleic acid molecules whose complementary strand hybridizes with a nucleic acid molecule from a) or b)

under stringent conditions and which encode a polypeptide which exhibits the biological function of a photoprotein;

d) nucleic acid molecules which differ from the nucleic acid molecules mentioned under c) due to the degeneracy of the genetic code;

e) nucleic acid molecules which exhibit a sequence homology with SEQ ID NO: 5 of at least 95% and encode a polypeptide which has the biological function of a photoprotein; and f) nucleic acid molecules which exhibit a sequence homology with SEQ ID NO: 5 of at least 80% and encode a polypeptide which has the biological function of a photoprotein.

The invention also relates to a nucleic acid which is as described in the preceding paragraphs and which contains a functional promoter 5' to the coding sequence.

The invention includes recombinant DNA or RNA vectors which contain the previously described nucleic acids.

Organisms which harbor a vector as previously described are likewise in accordance with the invention.

The invention also relates to oligonucleotides having more than 10 consecutive nucleotides which are identical or complementary to a constituent sequence of a nucleic acid molecule as described above.

The invention also relates to a polypeptide which is encoded by a nucleic acid sequence as described above.

The invention also relates to a method for expressing the abovementioned polypeptides in bacteria, viral cells, yeasts or eukaryotic cells or in in-vitro expression systems.

The invention likewise relates to a method for purifying/isolating a polypeptide according to the invention.

The invention likewise relates to peptides having more than 5 consecutive amino acids which are recognized immunologically by antibodies directed against the photoprotein mtClytin.

The invention furthermore relates to peptides having more than 5 consecutive amino acids which are recognized immunologically by antibodies directed against the photoprotein clytin-2.

The invention also relates to peptides having more than 5 consecutive amino acids which are recognized immunologically by antibodies directed against the signal or leader peptide disclosed by SEQ ID NO: 3.

The invention also relates to peptides having more than 5 consecutive amino acids which are recognized immunologically by antibodies directed against the photoprotein disclosed by SEQ ID NO: 6 (clytin-2).

The invention relates to the use of a nucleic acid according to the invention as a marker gene or reporter gene.

The invention also relates to the use of a photoprotein according to the invention as a label or reporter.

The invention furthermore relates to the use, as signal or leader sequence, of a nucleic acid which contains the sequence depicted as SEQ ID NO: 4 or a sequence having 60%, 65%, 70%, 75%, 80%, 85% or 90%, preferably having 95%, sequence identity with SEQ ID NO: 4.

The invention also relates to the use, as signal or leader peptide, of a peptide which contains the sequence depicted as SEQ ID NO: 3 or a sequence having 60%, 65%, 70%, 75%, 80%, 85% or 90%, preferably having 95%, sequence identity with SEQ ID NO: 3.

The invention likewise relates to the use, which is described in the two preceding paragraphs, for transporting proteins which are fused to the signal or leader peptide into cell organelles.

The invention also relates to the use which is described in the preceding paragraph, with the cell organelles being mitochondria.

The invention also relates to the use which is described in the preceding paragraph, with the cell organelles being the endoplasmic reticulum (ER).

The invention furthermore relates to the use of the nucleic acid sequence which is depicted as SEQ ID NO: 4 as a signal or leader sequence.

The invention also relates to the use of the peptide which is depicted as SEQ ID NO: 3 and which contains the depicted sequence as a signal or leader peptide.

The invention likewise relates to the use which is described in the two preceding paragraphs for transporting a protein which is fused to the signal or leader peptide into cell organelles.

The invention also relates to the use which is described in the preceding paragraph, with the cell organelles being mitochondria.

The invention also relates to the use which is described in the preceding paragraph, with the cell organelles being the endoplasmic reticulum (ER).

The invention likewise relates to the use of the polypeptides according to the invention as reporter proteins in searching for pharmacological active compounds.

Finally, the invention also relates to the use of the nucleic acids according to the invention as reporter genes in searching for pharmacological active compounds.

Expressing the Photoproteins of the Invention

The production of a molecule which, after the gene has been introduced into a suitable host cell, enables the foreign gene which is cloned into an expression vector to be transcribed and translated is termed expression. Expression vectors contain the control signals which are required for expressing genes in prokaryotic or eukaryotic cells.

In principle, expression vectors can be constructed in two different ways. In the case of what are termed transcription fusions, the protein encoded by the cloned-in foreign gene is synthesized as an authentic, biologically active protein. For this purpose, the expression vector carries all the 5' and 3' control signals which are required for the expression.

In the case of what are termed translation fusions, the protein encoded by the cloned-in foreign gene is expressed, together with another protein which can be detected readily, as a hybrid protein. The 5' and 3' control signals which are required for the expression, including the start codon and, possibly, a part of the sequences encoding the N-terminal regions of the hybrid protein to be formed, originate from the vector. The additional inserted protein moiety not only in many cases stabilizes the protein, which is encoded by the cloned-in foreign gene, against breakdown by cellular proteases; it can also be used for detecting and isolating the hybrid protein which is formed. The expression can take place either transiently or stably. Suitable host organisms are bacteria, yeasts, viruses or eukaryotic systems.

Purifying the Photoproteins of the Invention

The isolation of proteins (after they have been overexpressed as well) is frequently termed protein purification. A large number of established methods are available for purifying proteins.

The solid/liquid separation is a basic operation in connection with isolating proteins. This procedural step is required when separating cells from the culture medium, when clarifying the crude extract after having disrupted the cells and removing the cell debris, and when separating off sediments after precipitations, etc. It takes place by means of centrifugation and filtration.

In order to obtain intracellular proteins, the cell wall must be destroyed or rendered permeable. High-pressure homogenizers or agitator ball mills or glass bead mills are used for this purpose, depending on the scale and the organism. Mechanical cell integrations and ultrasonic treatment are used, inter alia, on the laboratory scale.

Both in the case of extracellular proteins and in the case of intracellular proteins (following cell disruption), various precipitation methods using salts (in particular ammonium sulfate) or organic solvents (alcohols or acetone) represent rapid and efficient methods for concentrating proteins. When intracellular proteins are being purified, it is desirable to remove the soluble nucleic acids (precipitation with, for example, streptomycin sulfate or protamine sulfate). When extracellular proteins are being isolated, carriers (e.g. starch or kieselguhr) are frequently added before adding the precipitating agents in order to obtain sediments which are easier to handle.

Numerous chromatographic methods and partition methods (absorption chromatography and ion exchange chromatography, gel filtration, affinity chromatography and electrophoreses) are available for high-degree purification. Column chromatography is also used on an industrial scale. Affinity chromatography, which makes possible purification factors of up to several 100 s per step, is especially important for the laboratory scale.

Extracellular proteins accrue in relatively dilute solutions. Just like extracellular proteins, they have to be concentrated before being subjected to further use. In addition to the methods which have already been mentioned, ultrafiltration has proved to be of value, on an industrial scale as well.

Inorganic salts which accompany proteins are frequently undesirable in the case of specific applications. They can be removed by, inter alia, gel filtration, dialysis and diafiltration.

A large number of proteins are used as dry preparations. Important drying methods are vacuum drying, freeze drying and spray drying.

Nucleotide and Amino Acid Sequences

The photoprotein mtClytin is encoded by the following nucleotide sequence (SEQ ID NO: 1):

```
5'-gacagataaaaaattcactccttagattatttagtgaataagagaaa
aaaaggataagaaatcaagatgcaaaggtttacaaatcgtcttctttcca
tgtcggctttacgtgcaagatcaagattgcaacgcacggcaaattttcac
accagcatactcttggctacagattcaaaatacgcggtcaaactcgatcc
tgattttgcaaatccaaaatggatcaacagacacaaatttatgttcaact
ttttggacataaacggtaaggggaaaatcacattagatgaaatcgtctcc
aaagcttcagacgacatttgtgctaaactggatgcaacaccagaacagac
caaacgtcaccaggatgctgttgaagccttttcaagaaaatgggcatgg
attatggtaaagaagttgcattcccagaatttattaagggatgggaagag
ttggccgaacacgacttggaactctggtctcaaaacaaaagtacattgat
ccgtgaatggggagatgctgttttcgacattttcgacaaagacgcaagtg
gctcaatcagtttagacgaatggaaggcttacggacgaatctctggaatc
tgtccatcagacgaagacgctgagaagacgttcaaacattgtgatttgga
caacagtggcaaacttgatgttgatgagatgaccaggcaacatttaggct
tctggtacacattggatccaacttctgatggtctttatggcaattttgtt
ccctaagaagcgttcagttaaaaacgctaaacattgttcagttgtaaaat
```

-continued

```
tatattcattttcatttcgtaaaattagtatttataaatttgtatcataa
attgtatccatgttgtagactaaataagactcggcaaaaaaaaaaaaaa
aaaaaaaaaaaaaa-3'.
```

This yields an amino acid sequence of (SEQ ID NO: 2):

```
MQRFTNRLLSMSALRARSRLQRTANFHTSILLATDSKYAVKLDPDFANPK
WINRHKFMFNFLDINGKGKITLDEIVSKASDDICAKLDATPEQTKRHQDA
VEAFFKKMGMDYGKEVAFPEFIKGWEELAEHDLELWSQNKSTLIREWGDA
VFDIFDKDASGSISLDEWKAYGRISGICPSDEDAEKTFKHCDLDNSGKLD
VDEMTRQHLGFWYTLDPTSDGLYGNFVP
```

The putative signal peptide of the photoprotein mtClytin possesses the following sequence (SEQ ID NO: 3):

```
MQRFTNRLLSMSALRA
``` and has the following nucleic acid sequence:

```
                                            (SEQ ID NO 4)
5'-atgcaaaggtttacaaatcgtcttctttccatgtcggctttacgtgc
a-3'
```

The photoprotein clytin-2 is encoded by the following nucleotide sequence (SEQ ID NO: 5):

```
5'-GATCTCAGCTCAACTTGCAATAAGTATCAGATCAAATTTTGCAACTC
AAAGCAAATCATCAACTTCATCATAATGACTGACACTGCTTCAAAATACG
CTGTCAAACTCAAGACCAACTTTGAAGATCCAAAATGGGTCAACAGACAC
AAATTTATGTTCAACTTTTTGGACATTAACGGCAACGGAAAAATCACTTT
GGATGAAATTGTCTCCAAAGCTTCGGATGACATTTGCGCCAAACTTGGAG
CTACACCAGCTCAAACCCAACGTCATCAGGAAGCTGTTGAAGCTTTCTTC
AAGAAGATTGGTTTGGATTATGGCAAAGAAGTCGAATTCCCAGCTTTCGT
TAACGGATGGAAAGAACTGGCCAAACATGACTTGAAACTTTGGTCCCAAA
ACAAGAAATCTTTGATCCGCAATTGGGGAGAAGCTGTATTCGACATTTTC
GACAAGGACGGAAGTGGCTCAATCAGTTTGGACGAATGGAAAACATACGG
AGGAATCTCTGGAATCTGTCCATCAGACGAAGACGCTGAAAAGACCTTCA
AACATTGCGATTTGGACAACAGTGGCAAACTTGATGTTGACGAGATGACC
AGACAACATTTGGGATTCTGGTACACCTTGGACCCTAACGCTGATGGTCT
TTATGGCAACTTTGTCCCTTAAAAACTTTTTTTGCTGTAAATTCTTTACG
GGTTATTTTTTCATAATTGTCATTTGATTTTAACTTTGTTTCGGAAAATG
AAAAATATTCTTTATTCAGAAAAAAAAAAAAAAAAAAAAAAAAA-3'
```

This yields an amino acid sequence of (SEQ ID NO: 6):

```
MTDTASKYAVKLKTNFEDPKWVNRHKFMFNFLDINGNGKITLDEIVSKAS
DDICAKLGATPAQTQRHQEAVEAFFKKIGLDYGKEVEFPAFVNGWKELAK
```

-continued
HDLKLWSQNKKSLIRNWGEAVFDIFDKDGSGSISLDEWKTYGGISGICPS

DEDAEKTFKHCDLDNSGKLDVDEMTRQHLGFWYTLDPNADGLYGNFVP

These sequences are reproduced in the sequence listing.

BRIEF DESCRIPTION OF THE FIGURES

FIG. 7 shows the alignment of clytin and mtClytin at the amino acid level.

FIG. 8 shows the alignment of clytin and mtClytin at the nucleic acid level.

FIG. 9 shows the alignment of clytin, mtClytin and clytin-2 at the amino acid level.

EXAMPLES

Example 1

The Clontech plasmid pTrip1Ex2 was used as vector for preparing the construct which is described below. The derivative of the vector was designated pTrip1Ex2-mtClytin. The vector pTrip1Ex2-mtClytin was used for expressing mtClytin in bacterial systems.

Figure 1:
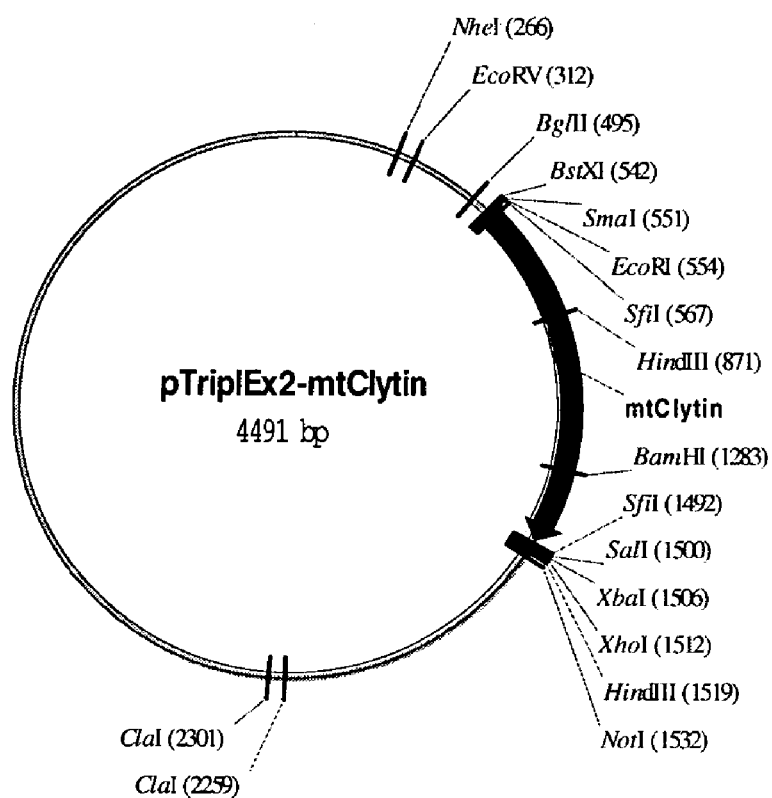
FIG. 1 shows the plasmid map of the vector pTrip1EX2-mtClytin.

FIG. 1 shows the plasmid map of the vector pTrip1EX2-mtClytin.

Example 2

The Clontech plasmid pcDNA3.1(+) was used as the vector for preparing the construct which is described below. The derivative of the vector was designated pcDNA3-mtClytin. The vector pcDNA3-mtClytin was used for expressing mtClytin in eukaryotic systems.

Figure 2:
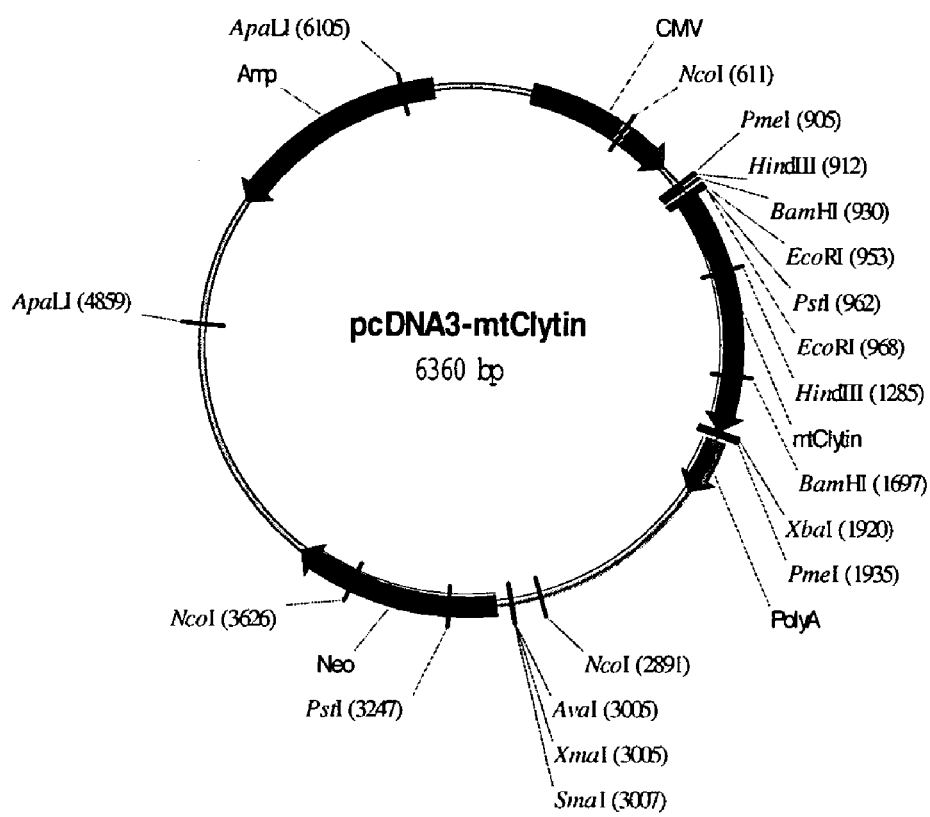
FIG. 2 shows the plasmid map of the vector pcDNA3-mtClytin.

FIG. 2 shows the plasmid map of the vector pcDNA3-mtClytin.

Example 3

Bacterial Expression

The bacterial expression was effected in the *E. coli* strain BL21(DE3) by transforming the bacteria with the expression plasmids pTrip1EX2-mtClytin and pTrip1EX2. The transformed bacteria were incubated at 37° C. for 3 hours in LB medium and the expression was induced for 4 hours by adding IPTG up to a final concentration of 1 mM. The induced bacteria were harvested by centrifugation, resuspended in 50 mM Tris/HCl (pH 9.0)+5 mM EDTA and disrupted by ultrasonication. The lysate was subsequently centrifuged at 13 000 rpm (16 000 ref) for 15 minutes and the supernatant removed. The supernatant (dilutions 1:5, 1:10; 1:20 and 1:50 with Tris/HCl pH 9.0)) was incubated with coelenterazine (10E-07 M coelenterazine in Tris/HCl pH 9.0) for 3 hours in the dark. The bioluminescence was measured in a luminometer directly after adding 5 mM calcium chloride. The measurement integration time was 40 seconds.

Figure 3:
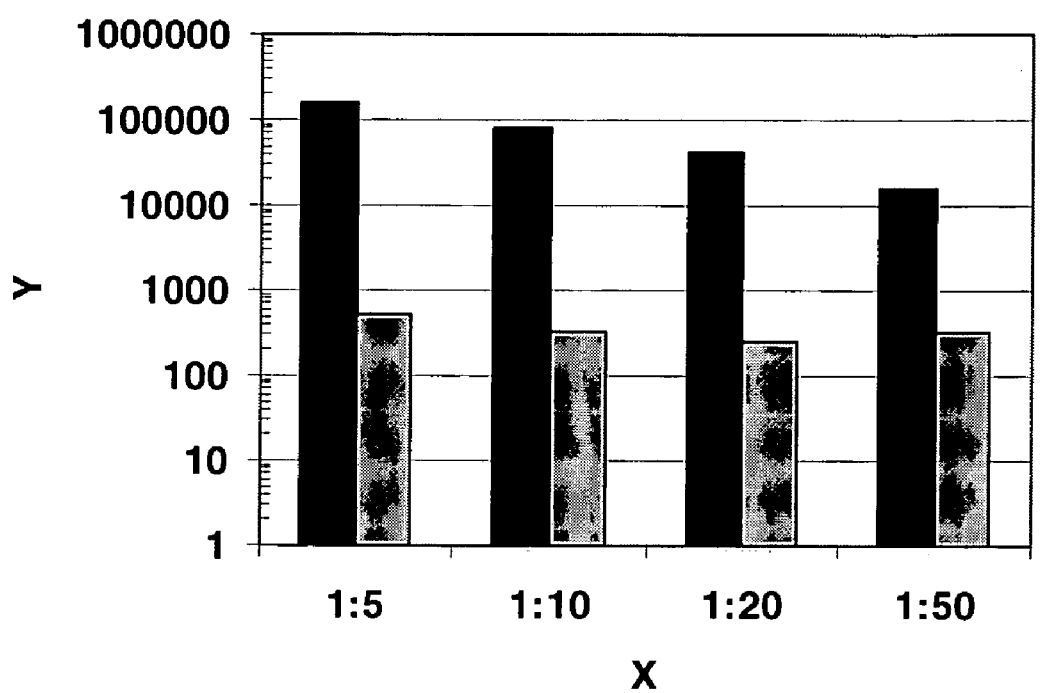
FIG. 3 shows the result of the bacterial expression of mtClytin and the bioluminescence activity of mtClytin following bacterial expression. (Y=RLU: relative light units; X=dilution; black bar=mtClytin; gray bar=control lysate).

FIG. 3 shows the results of measuring the bioluminescence of mtClytin in bacteria.

Example 4

Eukaryotic Expression

Constitutive eukaryotic expression was effected in CHO cells by transfecting the cells with the expression plasmids pcDNA3-mtClytin and pcDNA3.1(+) in transient experiments. For this, 10 000 cells per well were plated out, in DMEM-F12 medium, on 96-well microtiter plates and the plates were incubated overnight at 37° C. Transfection was effected using the Fugene 6 kits (Roche) in accordance with the manufacturer's instructions. The transfected cells were incubated overnight in DMEM-F12 medium at 37° C. The medium was then removed and replaced with 50 μl of coelenterazine (10E-07 M coelenterazine in PBS). The cells were incubated at 37° C. for 3 hours and ATP (adenosine triphosphate) was then added to a final concentration of 1 μM. The measurement in a luminometer was started directly after the addition. The integration time was 1 second, with the total measurement time being 60 seconds.

Figure 4:
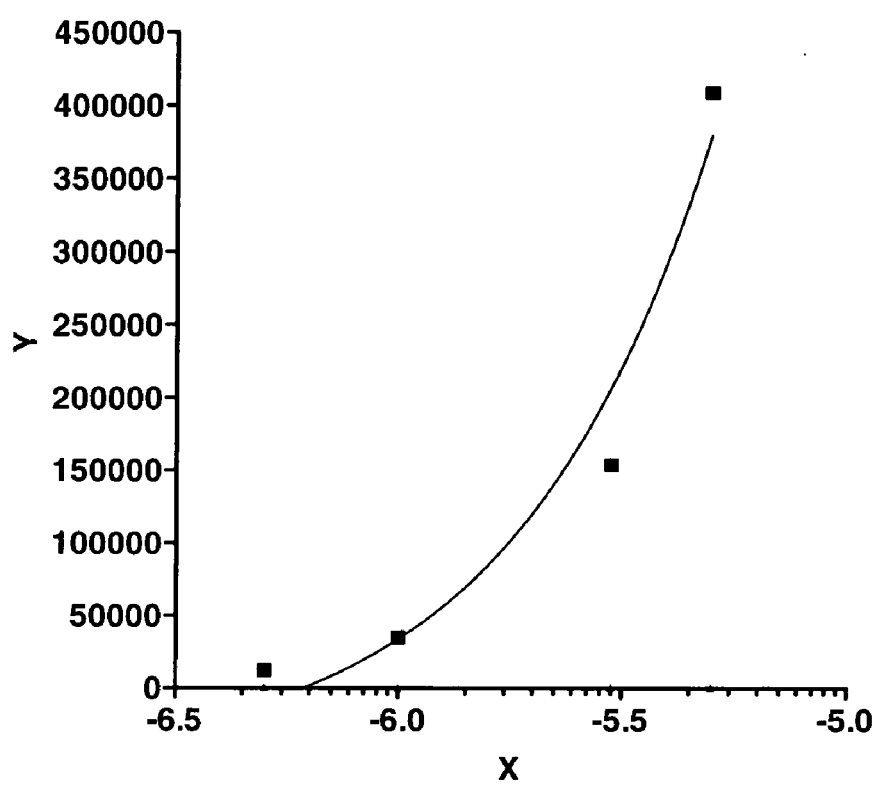
FIG. 4 shows the result of the eukaryotic expression of mtClytin and the bioluminescence activity of mtClytin following expression in CHO cells. (Y=RLU: relative light units; X=ATP (logarithmic representation in mol/l)).

FIG. 4 shows the results of measuring the bioluminescence of mtClytin in CHO cells.

Example 5

BLAST

Result of a BLAST Analysis of mtClytin at the Amino Acid Level:

>emb|CAD87655.1| unnamed protein product [*Clytia gregaria*], Length=198, Score=368 bits (945), Expect=e-101, Identities=171/195 (87%), Positives=182/195 (92%)

>sp|Q08121|CLYT_CLYGR Clytin precursor (Phialidin), pir||S28860 clytin-hydromedusa (Clytia gregaria), emb-|CAA49754.1| clytin [*Clytia gregaria*], gb|AAA28293.1| apoclytin, Length=198, Score=368 bits (945), Expect=e-101, Identities=171/195 (87%), Positives=182/195 (92%)

>emb|CAD87658.1| unnamed protein product [synthetic construct], Length=198, Score=367 bits (943), Expect=e-101, Identities=170/195 (87%), Positives=182/195 (93%)

>sp|Q27709|OBL_OBELO Obelin precursor (OBL), pdb|1EL4|A Chain A, Structure Of The Calcium-Regulated Photoprotein Obelin, Determined By Sulfur Sas, gb|AAA67708.1| unnamed protein product, Length=195, Score=327 bits (837), Expect=1e-88, Identities=150/193 (77%), Positives=170/193 (87%)

>emb|CAD87674.1| unnamed protein product [synthetic construct], Length=195, Score=326 bits (835), Expect=2e-88, Identities=149/193 (77%), Positives=170/193 (87%)

>emb|CAD87672.1| unnamed protein product [synthetic construct], Length=195, Score=325 bits (834), Expect=3e-88, Identities=149/193 (77%), positives=170/193 (87%)

>emb|CAD87673.1| unnamed protein product [synthetic construct], Length=195, Score=325 bits (833), Expect=4e-88, Identities=149/193 (77%), Positives=170/193 (87%)

>pdb|1JF0|A Chain A, The Crystal Structure Of Obelin From Obelia Geniculata At 1.82 A Resolution, gb|AAL86372.1|AF394688_1 apoobelin [*Obelia geniculata*], Length=195, Score=325 bits (833), Expect=4e-88, Identities=149/193 (77%), Positives=168/193 (86%)

Example 6

BLAST

Result of a BLAST Analysis of mtClytin at the Nucleic Acid Level:

>emb|AX702125.1| Sequence 23 from Patent WO03006497, Length=597, Score=669 bits (348), Expect=0.0, Identities=504/582 (86%)

>emb|AX702119.1|Sequence 17 from Patent WO03006497, Length=597, Score=669 bits (348), Expect=0.0, Identities=504/582 (86%)

>emb|X70221.1|CGCLYTIN *C. gregaria* mRNA for clytin, Length=747, Score=669 bits (348), Expect=0.0, Identities=504/582 (86%)

>gb|L13247.1|CY1APOCLYT *Clytia gregaria* apoclytin mRNA, complete cds, Length=747, Score=669 bits (348), Expect=0.0, Identities=504/582 (86%)

>emb|AX702187.1| Sequence 85 from Patent WO03006497, Length=597, Score=664 bits (345), Expect=0.0, Identities=503/582 (86%)

>emb|AX702185.1| Sequence 83 from Patent WO03006497, Length=597, Score=664 bits (345), Expect=0.0, Identities=503/582 (86%)

>emb|AX702183.1| Sequence 81 from Patent WO03006497, Length=597, Score=664 bits (345), Expect=0.0, Identities=503/582 (86%)

>emb|AX702181.1| Sequence 79 from Patent WO03006497, Length=597, Score=664 bits (345), Expect=0.0, Identities=503/582 (86%)

>emb|AX702179.1| Sequence 77 from Patent WO03006497, Length=597, Score=664 bits (345), Expect=0.0, Identities=503/582 (86%)

>emb|AX702131.1| Sequence 29 from Patent WO03006497, Length=597, Score=664 bits (345), Expect=0.0, Identities=503/582 (86%)

>emb|AX702129.1| Sequence 27 from Patent WO03006497, Length=597, Score=664 bits (345), Expect=0.0, Identities=503/582 (86%)

Example 7

FIG. 7 shows the alignment of mtClytin with clytin (*Clytia gregaria*) at the nucleic acid level.

Example 8

FIG. 8 shows the alignment of mtClytin with clytin (*Clytia gregaria*) at the amino acid level.

Example 9

Kinetic Analysis of mtClytin

For the kinetic analysis of the bioluminescence of mtClytin, CHO cells were transiently transfected with pcDNA3-mtClytin or pcDNA-obelin or pcDNA3 (without any integrated cDNA). The transfection and measurement were carried out as described in Example 4. The readings were taken for a period of 60 seconds using an integration time of 1 second.

Figure 5:
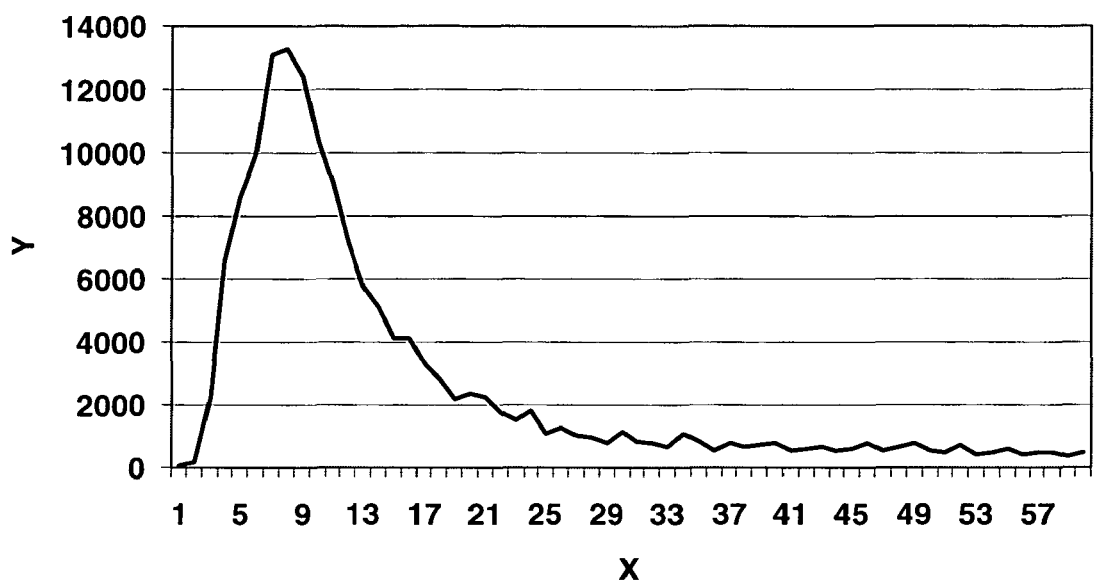
FIG. 5 shows the kinetic analysis of the bioluminescence of mtClytin. (Y=RLU: relative light units; X=time [seconds]).
Figure 6:
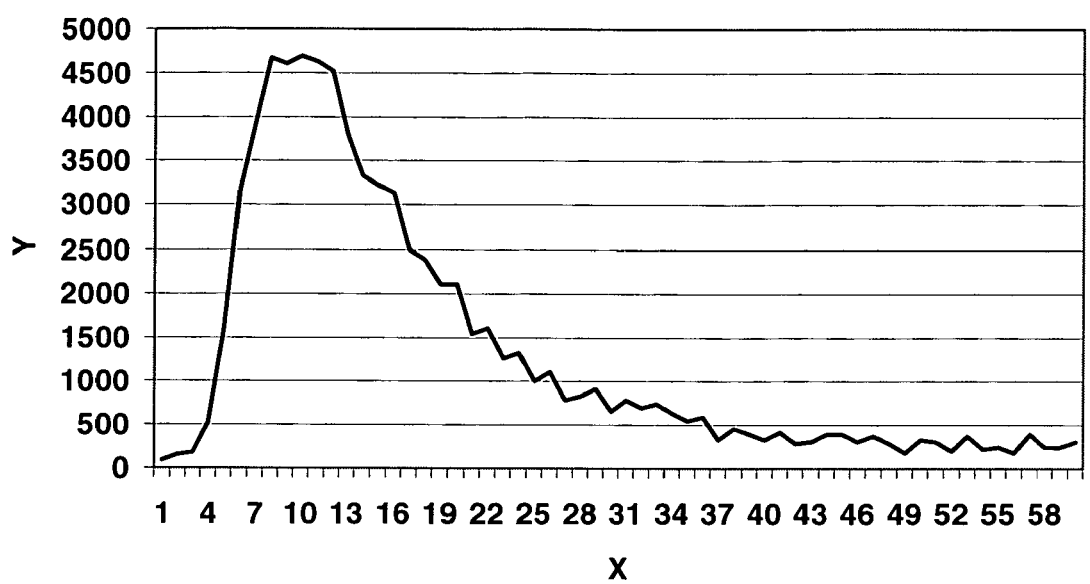
FIG. 6 shows the kinetic analysis of the bioluminescence of obelin. (Y=RLU: relative light units; X=time [seconds]).

FIGS. 5 and 6 show the results of the kinetic analysis of mtClytin and obelin.

Example 10

MITOPROT Analysis

The computer program MITOPROT was used to analyze the mtClytin signal peptide (Claros et al., 1996). The following photoproteins were analyzed: obelin (Q27709), aequorin (P07164), clytin (Q08121) and mtClytin (SEQ ID NO: 2).

Results of the analyses:

| Obelin: | | | | |
|---|---|---|---|---|
| Sequence name: OBELIN | | | | |
| Input sequence length: 195 aa | | | | |
| VALUES OF COMPUTED PARAMETERS | | | | |
| Net charge of query sequence | | | −11 | |
| Analysed region | | | 11 | |
| Number of basic residues in targeting sequence | | | 3 | |
| Number of acidic residues in targeting sequence | | | 0 | |
| Cleavagesite | | | not predictable | |
| Cleaved sequence | | | — | |
| HYDROPHOBIC SCALE USED | | | | |
| | GES | KD | GVH1 | ECS |
| H17 | −0.624 | 0.259 | −0.308 | 0.295 |
| MesoH | −1.573 | −0.241 | −0.642 | 0.060 |
| MuHd_075 | 14.019 | 3.641 | 4.408 | 1.523 |
| MuHd_095 | 7.994 | 7.898 | 3.285 | 1.838 |
| MuHd_100 | 13.734 | 9.836 | 5.597 | 2.742 |
| MuHd_105 | 21.195 | 11.755 | 7.339 | 4.117 |
| Hmax_075 | −9.450 | −2.800 | −4.008 | 1.132 |
| Hmax_095 | −0.963 | 1.837 | −1.971 | 1.103 |
| Hmax_100 | 0.400 | 1.300 | −1.942 | 2.240 |
| Hmax_105 | 10.617 | 6.067 | 0.733 | 3.127 |

-continued

| PROBABILITY |
| --- |
| of export to mitochondria: 0.1479 |

Aequorin:

Sequence name: AEQUORIN
Input sequence length: 196 aa

VALUES OF COMPUTED PARAMETERS

| | |
| --- | --- |
| Net charge of query sequence | −13 |
| Analysed region | 3 |
| Number of basic residues in targeting sequence | 0 |
| Number of acidic residues in targeting sequence | 0 |
| Cleavage site | not predictable |
| Cleaved sequence | — |

HYDROPHOBIC SCALE USED

| | GES | KD | GVH1 | ECS |
| --- | --- | --- | --- | --- |
| H17 | 0.006 | 0.794 | −0.263 | 0.368 |
| MesoH | −1.673 | −0.382 | −0.703 | 0.048 |
| MuHd_075 | 24.326 | 4.153 | 5.947 | 2.450 |
| MuHd_095 | 12.638 | 7.213 | 4.218 | 1.796 |
| MuHd_100 | 13.748 | 8.827 | 4.477 | 2.427 |
| MuHd_105 | 16.581 | 11.426 | 5.056 | 3.453 |
| Hmax_075 | 0.438 | 0.233 | −2.490 | 1.692 |
| Hmax_095 | 0.525 | −1.400 | −2.394 | 0.674 |
| Hmax_100 | −0.100 | −1.200 | −2.292 | 1.550 |
| Hmax_105 | 0.500 | −0.000 | −2.164 | 1.540 |

| PROBABILITY |
| --- |
| of export to mitochondria: 0.0148 |

Clytin:

Sequence name: CLYTIN
Input sequence length: 198 aa

VALUES OF COMPUTED PARAMETERS

| | |
| --- | --- |
| Net charge of query sequence | −9 |
| Analysed region | 32 |
| Number of basic residues in targeting sequence | 6 |
| Number of acidic residues in targeting sequence | 2 |
| Cleavage site | not predictable |
| Cleaved sequence | — |

HYDROPHOBIC SCALE USED

| | GES | KD | GVH1 | ECS |
| --- | --- | --- | --- | --- |
| H17 | −0.429 | 0.341 | −0.313 | 0.313 |
| MesoH | −1.778 | −0.307 | −0.718 | 0.053 |
| MuHd_075 | 32.928 | 17.509 | 7.351 | 5.708 |
| MuHd_095 | 30.874 | 20.344 | 9.074 | 5.834 |
| MuHd_100 | 36.596 | 22.666 | 10.051 | 6.762 |
| MuHd_105 | 39.174 | 19.336 | 10.379 | 7.609 |
| Hmax_075 | 4.900 | 7.087 | −1.223 | 3.684 |
| Hmax_095 | 13.600 | 10.100 | 1.251 | 4.390 |
| Hmax_100 | 14.000 | 12.600 | 1.601 | 5.060 |
| Hmax_105 | 6.650 | 13.067 | −0.468 | 3.920 |

| PROBABILITY |
| --- |
| of export to mitochondria: 0.2047 | clytin-2:

Sequence name: CLYTIN-2
Input sequence length: 198 aa

VALUES OF COMPUTED PARAMETERS

| | |
| --- | --- |
| Net charge of query sequence | −7 |
| Analysed region | 16 |

-continued

| | |
|---|---|
| Number of basic residues in targeting sequence | 3 |
| Number of acidic residues in targeting sequence | 1 |
| Cleavage site | not predictable |
| Cleaved sequence | — |

| HYDROPHOBIC SCALE USED | | | | |
|---|---|---|---|---|
| | GES | KD | GVH1 | ECS |
| H17 | −0.288 | 0.341 | −0.213 | 0.313 |
| MesoH | −1.519 | −0.206 | −0.681 | 0.081 |
| MuHd_075 | 32.594 | 15.092 | 8.192 | 4.075 |
| MuHd_095 | 36.090 | 19.707 | 8.836 | 6.716 |
| MuHd_100 | 38.617 | 20.269 | 9.682 | 6.851 |
| MuHd_105 | 30.267 | 16.082 | 8.229 | 5.470 |
| Hmax_075 | 6.533 | 6.417 | −0.793 | 2.508 |
| Hmax_095 | 13.600 | 10.100 | 1.251 | 4.390 |
| Hmax_100 | 13.600 | 10.100 | 1.251 | 4.390 |
| Hmax_105 | 13.417 | 10.150 | 1.612 | 3.862 |

PROBABILITY of export to mitochondria: 0.3974 mtClytin:

Sequence name: mtClytin
Input sequence length: 228 aa

| VALUES OF COMPUTED PARAMETERS | |
|---|---|
| Net charge of query sequence | −8 |
| Analysed region | 34 |
| Number of basic residues in targeting sequence | 6 |
| Number of acidic residues in targeting sequence | 0 |
| Cleavage site | 17 |
| Cleaved sequence | MQRFTNRLLSMSALRA |

| HYDROPHOBIC SCALE USED | | | | |
|---|---|---|---|---|
| | GES | KD | GVH1 | ECS |
| H17 | −0.135 | 0.453 | −0.343 | 0.309 |
| MesoH | −1.623 | −0.215 | −0.701 | 0.073 |
| MuHd_075 | 33.394 | 19.322 | 8.634 | 7.593 |
| MuHd_095 | 34.726 | 19.634 | 8.110 | 8.861 |
| MuHd_100 | 32.825 | 16.596 | 7.376 | 7.520 |
| MuHd_105 | 28.005 | 19.893 | 7.410 | 7.865 |
| Hmax_075 | 16.683 | 17.733 | 2.851 | 5.763 |
| Hmax_095 | 13.125 | 13.388 | 2.299 | 4.314 |
| Hmax_100 | 8.300 | 11.500 | 1.845 | 3.830 |
| Hmax_105 | 1.700 | 9.500 | −1.171 | 2.390 |

PROBABILITY of export to mitochondria: 0.9974

The probability of a translocation of the analyzed peptide into mitochondria increases as the calculated factor approaches 1.

The analysis of the protein sequences of obelin, aequorin, clytin, clytin-2 and mtClytin has shown that only mtClytin has the features of a protein which can be transported into mitochondria.

Example 11

FIG. 9 shows the alignment of mtClytin, clytin (*Clytia gregaria*) and clytin-type2 at the amino acid level.

Literature/Patents
U.S. Pat. No. 6,495,355
U.S. Pat. No. 5,541,309
U.S. Pat. No. 5,093,240
US-0908909
U.S. Pat. No. 6,152,358
JP-0176125
GB-0024357
WO03006497
WO200168824

Alam J, Cook J L. Reporter genes: application to the study of mammalian gene transcription. *Anal Biochem.* 1990 Aug. 1; 188(2):245-54

Altschul, Stephen F., Thomas L. Madden, Alejandro A. Schäffer, Jinghui Zhang, Zheng Zhang, Webb Miller, and David J. Lipman (1997); Gapped BLAST and PSI-BLAST: a new generation of protein database search programs; *Nucleic Acids Res.* 25:3389-3402

Chiesa A, Rapizzi E, Tosello V, Pinton P, de Virgilio M, Fogarty K E, Rizzuto R. Recombinant aequorin and green fluorescent protein as valuable tools in the study of cell signalling. *Biochem J. Apr.* 1, 2001; 355(Pt 1): 1-12.

Claros, M. G., Vincens, P. (1996); Computational method to predict mitochondrially imported proteins and their targeting seqeunces. *Eur. J. Biochem* 241, 779-786.

Cullen Bryan R., Malim Michael H., Secreted placental alkaline phosphatase as a eukaryotic reporter gene. *Methods in Enzymology.* 216:362ff Fagan T F, Ohmiya Y, Blinks J R, Inouye S, Tsuji F I. Cloning, expression and sequence analysis of cDNA for the Ca(2+)-binding photoprotein, mitrocomin. *FEBS Lett. Nov.* 1, 1993; 333(3):301-5

Hastings, J. W. and Morin, J. G. (1969) Comparative biochemistry of calcium-activated photoproteins from the ctenophore, *Mnemiopsis* and the coelenterates *Aequorea, Obelia*, and *Pelagia. Biol. Bull.* 137, 402.

Haddock S H, Rivers T J, Robison B H. Can coelenterates make coelenterazine? Dietary requirement for luciferin in cnidarian bioluminescence. *Proc Natl Acad Sci USA Sep.* 25, 2001; 98(20): 1, 1148-51

Inouye S, Tsuji F I. (1994) Aequorea green fluorescent protein. Expression of the gene and fluorescence characteristics of the recombinant protein. *FEBS Lett* 1994 Mar. 21; 341(2-3):277-80

Inouye S, Tsuji F I. Cloning and sequence analysis of cDNA for the Ca(2+)-activated photoprotein, clytin. *FEBS Lett. Jan.* 11, 1993; 315(3):343-6.

Illarionov B A, Bondar V S, Illarionova V A, Vysotski E S. Sequence of the cDNA encoding the Ca(2+)-activated photoprotein obelin from the hydroid polyp Obelia longissima. *Gene. Feb.* 14, 1995; 153(2):273-4.

Jones K, Hibbert F, Keenan M. Glowing jellyfish, luminescence and a molecule called coelenterazine. *Trends Biotechnol December* 1999; 17(12):477-81

Johnson, F. H., Shimomura, O., Saiga, Y., Gershman, L. C., Reynolds, G. T., and Waters, J. R. (1962) Quantum efficiency of *Cypridina* luminescence, with a note on that of Aequorea. *J. Cell. Comp. Physiol.* 60, 85-103.

Morin, J. G. and Hastings, J. W. (1971) Biochemistry of the bioluminescence of colonial hydroids and other coelenterates. *J. Cell. Physiol.* 77, 305-311.

Phillips G N. Structure and dynamics of green fluorescent protein. *Curr Opin Struct Biol. December* 1997; 7(6):821-7

Sambrook, J., Fritsch, E. Maniatis, T. 1989, Molecular cloning. A laboratory manual Vol 1-3, *Cold Spring Harbor*, New York: Cold Spring Harbor Laboratory Press Shimomura O., Johnson F H. Properties of the bioluminescent protein aequorin. *Biochemistry* 969 ct;8(10):3991-7

Shimomura O., Bioluminescence in the sea: photoprotein systems. *Symp Soc Exp Biol.* 1985; 39:351-72

Shimomura O. Isolation and properties of various molecular forms of aequorin. *Biochem J. Mar.* 1, 1986; 234(2):271-7.

Snowdowne K W, Borle A B. Measurement of cytosolic free calcium in mammalian cells with aequorin. *Am J Physiol. November* 1984; 247(5 Pt 1):C396-408.

Ward, W. W. (1998) Biochemical and physical properties of green fluorescent protein. In: *Green Fluorescent Protein: Properties, Applications, and Protocols* (Chalfie, M. and Kain, S., eds) pp. 45-70. Wiley-Liss, Inc.

Yang Te-Tuan, Sinai Parisa, Kitts Paul A. Kain Seven R., Quantification of gene expression with a secreted alkaline phosphatase reporter system. *Biotechnique.* 1997 23(6) 1110ff

The invention claimed is:

1. An isolated nucleic acid molecule which is selected from the group consisting of:
   a) a nucleic acid molecule which encodes a polypeptide which contains the amino acid sequence disclosed by SEQ ID NO: 2;
   b) a nucleic acid molecule which contains the sequence depicted by SEQ ID NO: 1;
   c) a nucleic acid molecule which exhibits a sequence identity along its full length with SEQ ID NO: 1 of at least 95% and encodes a polypeptide which has the biological function of a photoprotein; and
   d) a nucleic acid molecule which exhibits a sequence identity along its full length with SEQ ID NO: 1 of at least 65% and encodes a polypeptide which has the biological function of a photoprotein.

2. The nucleic acid as claimed in claim 1, further comprising a nucleic acid encoding a polypeptide other than that encoded by the nucleic acid of claim 1, wherein a fusion gene is formed and wherein said fusion gene functions as a marker gene or reporter gene.

3. The nucleic acid as claimed in claim 1, wherein said nucleic acid functions as a reporter gene in searching for pharmacologically active compounds.

4. The nucleic acid as claimed in claim 1, which contains a functional promoter 5' to its coding sequence.

5. A recombinant DNA or RNA vector which contains the nucleic acid as claimed in claim 4.

6. An organism which harbors the vector as claimed in claim 5.

7. An isolated polypeptide which is encoded by a nucleic acid sequence as claimed in claim 1.

8. The polypeptide as claimed in claim 7, wherein said polypeptide functions as a reporter protein in searching for pharmacologically active compounds.

9. The polypeptide of claim 7, wherein said polypeptide is coupled to an additional protein.

10. The polypeptide of claim 9, wherein said additional protein is selected from the group consisting of: an antibiotic, an enzyme, a receptor, an antibody and an ion channel.

11. A method for producing a polypeptide having phosphoprotein activity, said method comprising placing the nucleic acid of claim 1 into a bacteria, a viral system, yeast or a eukaryotic cell or in an in-vitro expression system under conditions that express said nucleic acid, and thereby producing said polypeptide.

12. A polypeptide encoded by the nucleic acid of claim 2, wherein said polypeptide functions as a marker or reporter.

* * * * *

SEQUENCE LISTING

<160> NUMBER OF SEQ ID NOS: 9

<210> SEQ ID NO 1
<211> LENGTH: 912
<212> TYPE: DNA
<213> ORGANISM: Clytia gregaria

<400> SEQUENCE: 1

```
gacagataaa aaattcactc cttagattat ttagtgaata agagaaaaaa aggataagaa      60
atcaagatgc aaaggtttac aaatcgtctt ctttccatgt cggctttacg tgcaagatca     120
agattgcaac gcacggcaaa tttcacacc agcatactct tggctacaga ttcaaaatac     180
gcggtcaaac tcgatcctga ttttgcaaat ccaaaatgga tcaacagaca caaatttatg     240
ttcaactttt tggacataaa cggtaagggg aaaatcacat tagatgaaat cgtctccaaa     300
gcttcagacg acatttgtgc taaactggat gcaacaccag aacagaccaa acgtcaccag     360
gatgctgttg aagccttttt caagaaaatg ggcatggatt atggtaaaga agttgcattc     420
ccagaattta ttaagggatg ggaagagttg gccgaacacg acttggaact ctggtctcaa     480
aacaaaagta cattgatccg tgaatgggga gatgctgttt tcgacatttt cgacaaagac     540
gcaagtggct caatcagttt agacgaatgg aaggcttacg gacgaatctc tggaatctgt     600
ccatcagacg aagacgctga gaagacgttc aaacattgtg atttggacaa cagtggcaaa     660
cttgatgttg atgagatgac caggcaacat ttaggcttct ggtacacatt ggatccaact     720
tctgatggtc tttatggcaa ttttgttccc taagaagcgt tcagttaaaa acgctaaaca     780
```

```
ttgttcagtt gtaaaattat attcattttc atttcgtaaa attagtattt ataaatttgt    840
atcataaatt gtatccatgt tgtagactaa ataagactcg gcaaaaaaaa aaaaaaaaaa    900
aaaaaaaaaa aa                                                        912
```

<210> SEQ ID NO 2
<211> LENGTH: 228
<212> TYPE: PRT
<213> ORGANISM: Clytia gregaria

<400> SEQUENCE: 2

```
Met Gln Arg Phe Thr Asn Arg Leu Leu Ser Met Ser Ala Leu Arg Ala
1               5                   10                  15

Arg Ser Arg Leu Gln Arg Thr Ala Asn Phe His Thr Ser Ile Leu Leu
            20                  25                  30

Ala Thr Asp Ser Lys Tyr Ala Val Lys Leu Asp Pro Asp Phe Ala Asn
        35                  40                  45

Pro Lys Trp Ile Asn Arg His Lys Phe Met Phe Asn Phe Leu Asp Ile
    50                  55                  60

Asn Gly Lys Gly Lys Ile Thr Leu Asp Glu Ile Val Ser Lys Ala Ser
65                  70                  75                  80

Asp Asp Ile Cys Ala Lys Leu Asp Ala Thr Pro Glu Gln Thr Lys Arg
                85                  90                  95

His Gln Asp Ala Val Glu Ala Phe Phe Lys Lys Met Gly Met Asp Tyr
            100                 105                 110

Gly Lys Glu Val Ala Phe Pro Glu Phe Ile Lys Gly Trp Glu Glu Leu
        115                 120                 125

Ala Glu His Asp Leu Glu Leu Trp Ser Gln Asn Lys Ser Thr Leu Ile
    130                 135                 140

Arg Glu Trp Gly Asp Ala Val Phe Asp Ile Phe Asp Lys Asp Ala Ser
145                 150                 155                 160

Gly Ser Ile Ser Leu Asp Glu Trp Lys Ala Tyr Gly Arg Ile Ser Gly
                165                 170                 175

Ile Cys Pro Ser Asp Glu Asp Ala Glu Lys Thr Phe Lys His Cys Asp
            180                 185                 190

Leu Asp Asn Ser Gly Lys Leu Asp Val Asp Glu Met Thr Arg Gln His
        195                 200                 205

Leu Gly Phe Trp Tyr Thr Leu Asp Pro Thr Ser Asp Gly Leu Tyr Gly
    210                 215                 220

Asn Phe Val Pro
225
```

<210> SEQ ID NO 3
<211> LENGTH: 16
<212> TYPE: PRT
<213> ORGANISM: Clytia gregaria

<400> SEQUENCE: 3

```
Met Gln Arg Phe Thr Asn Arg Leu Leu Ser Met Ser Ala Leu Arg Ala
1               5                   10                  15
```

<210> SEQ ID NO 4
<211> LENGTH: 48
<212> TYPE: DNA
<213> ORGANISM: Clytia gregaria

<400> SEQUENCE: 4

```
atgcaaaggt ttacaaatcg tcttcttttcc atgtcggctt tacgtgca              48
```

<210> SEQ ID NO 5
<211> LENGTH: 791
<212> TYPE: DNA
<213> ORGANISM: Clytia gregaria

<400> SEQUENCE: 5

```
gatctcagct caacttgcaa taagtatcag atcaaatttt gcaactcaaa gcaaatcatc     60
aacttcatca taatgactga cactgcttca aaatacgctg tcaaactcaa gaccaacttt    120
gaagatccaa aatgggtcaa cagacacaaa tttatgttca acttttggga cattaacggc    180
aacggaaaaa tcactttgga tgaaattgtc tccaaagctt cggatgacat ttgcgccaaa    240
cttggagcta caccagctca aacccaacgt catcaggaag ctgttgaagc tttcttcaag    300
aagattggtt tggattatgg caaagaagtc gaattcccag cttttcgttaa cggatggaaa    360
gaactggcca acatgacttt gaaactttgg tcccaaaaca gaaatctttt gatccgcaat    420
tggggagaag ctgtattcga catttttcgac aaggacggaa gtggctcaat cagtttggac    480
gaatggaaaa catacggagg aatctctgga atctgtccat cagacgaaga cgctgaaaag    540
accttcaaac attgcgattt ggacaacagt ggcaaacttg atgttgacga gatgaccaga    600
caacatttgg gattctggta ccccttggac cctaacgctg atggtcttta tgcaacttt     660
gtcccttaaa aactttttt gctgtaaatt ctttacgggt tattttttca taattgtcat    720
ttgatttaa ctttgtttcg gaaaatgaaa aatattctt attcagaaaa aaaaaaaaa     780
aaaaaaaaa a                                                          791
```

<210> SEQ ID NO 6
<211> LENGTH: 198
<212> TYPE: PRT
<213> ORGANISM: Clytia gregaria

<400> SEQUENCE: 6

```
Met Thr Asp Thr Ala Ser Lys Tyr Ala Val Lys Leu Lys Thr Asn Phe
1               5                   10                  15

Glu Asp Pro Lys Trp Val Asn Arg His Lys Phe Met Phe Asn Phe Leu
            20                  25                  30

Asp Ile Asn Gly Asn Gly Lys Ile Thr Leu Asp Glu Ile Val Ser Lys
        35                  40                  45

Ala Ser Asp Asp Ile Cys Ala Lys Leu Gly Ala Thr Pro Ala Gln Thr
    50                  55                  60

Gln Arg His Gln Glu Ala Val Glu Ala Phe Phe Lys Lys Ile Gly Leu
65                  70                  75                  80

Asp Tyr Gly Lys Glu Val Glu Phe Pro Ala Phe Val Asn Gly Trp Lys
                85                  90                  95

Glu Leu Ala Lys His Asp Leu Lys Leu Trp Ser Gln Asn Lys Lys Ser
            100                 105                 110

Leu Ile Arg Asn Trp Gly Glu Ala Val Phe Asp Ile Phe Asp Lys Asp
        115                 120                 125

Gly Ser Gly Ser Ile Ser Leu Asp Glu Trp Lys Thr Tyr Gly Gly Ile
    130                 135                 140

Ser Gly Ile Cys Pro Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
```

```
                180              185                190
Tyr Gly Asn Phe Val Pro
            195

<210> SEQ ID NO 7
<211> LENGTH: 747
<212> TYPE: DNA
<213> ORGANISM: Clytia gregaria

<400> SEQUENCE: 7
atcaactttt gcaactcaaa gcaaatttca aaacttcaac atggctgaca ctgcatcaaa      60
atacgccgtc aaactcagac ccaacttcga caacccaaaa tgggtcaaca gacacaaatt     120
tatgttcaac ttttggaca ttaacggcga cggaaaaatc actttggatg aaatcgtctc     180
caaagcttcg gatgacattt gcgccaaact tggagcaaca ccagaacaga ccaaacgtca     240
ccaggatgct gtcgaagctt tcttcaaaaa gattggtatg gattatggta agaagtcga      300 attcccagct tttgttgatg gatggaaaga actggccaat tatgacttga aactttggtc     360
tcaaaacaag aaatctttga tccgcgactg gggagaagct gttttcgaca ttttgacaa      420 agacggaagt ggctcaatca gtttggacga atggaaggct tatggacgaa tctctggaat     480
ctgctcatca gacgaagacg ccgaaaagac cttcaaacat tgcgatttgg acaacagtgg     540
caaacttgat gttgatgaga tgaccagaca acatttggga ttctggtaca ccttggaccc     600
caacgctgat ggtctttacg gcaattttgt tccttaaaca tcgaaacaaa agcccaaaag     660
aagttttgga agaattattt gatactatca tttgttacta tttcgtaaca tgctatattt     720
tgtaacatgc tatatttaaa taatttt                                         747

<210> SEQ ID NO 8
<211> LENGTH: 198
<212> TYPE: PRT
<213> ORGANISM: Clytia gregaria

<400> SEQUENCE: 8

Met Ala Asp Thr Ala Ser Lys Tyr Ala Val Lys Leu Arg Pro Asn Phe
1               5                   10                  15

Asp Asn Pro Lys Trp Val Asn Arg His Lys Phe Met Phe Asn Phe Leu
            20                  25                  30

Asp Ile Asn Gly Asp Gly Lys Ile Thr Leu Asp Glu Ile Val Ser Lys
        35                  40                  45

Ala Ser Asp Asp Ile Cys Ala Lys Leu Gly Ala Thr Pro Glu Gln Thr
    50                  55                  60

Lys Arg His Gln Asp Ala Val Glu Ala Phe Phe Lys Lys Ile Gly Met
65                  70                  75                  80

Asp Tyr Gly Lys Glu Val Glu Phe Pro Ala Phe Val Asp Gly Trp Lys
                85                  90                  95

Glu Leu Ala Asn Tyr Asp Leu Lys Leu Trp Ser Gln Asn Lys Lys Ser
            100                 105                 110

Leu Ile Arg Asp Trp Gly Glu Ala Val Phe Asp Ile Phe Asp Lys Asp
        115                 120                 125

Gly Ser Gly Ser Ile Ser Leu Asp Glu Trp Lys Ala Tyr Gly Arg Ile
    130                 135                 140

Ser Gly Ile Cys Ser Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175
```

```
Gln His Leu Gly Phe Trp Tyr Thr Leu Asp Pro Asn Ala Asp Gly Leu
            180                 185             190

Tyr Gly Asn Phe Val Pro
        195

<210> SEQ ID NO 9
<211> LENGTH: 198
<212> TYPE: PRT
<213> ORGANISM: Clytia gregaria

<400> SEQUENCE: 9

Met Thr Asp Thr Ala Ser Lys Tyr Ala Val Lys Leu Lys Thr Asn Phe
1               5                   10                  15

Glu Asp Pro Lys Trp Val Asn Arg His Lys Phe Met Phe Asn Phe Leu
            20                  25                  30

Asp Ile Asn Gly Asn Gly Lys Ile Thr Leu Asp Glu Ile Val Ser Lys
            35                  40                  45

Ala Ser Asp Asp Ile Cys Ala Lys Leu Gly Ala Thr Pro Ala Gln Thr
    50                  55                  60

Gln Arg His Gln Glu Ala Val Glu Ala Phe Phe Lys Lys Ile Gly Leu
65                  70                  75                  80

Asp Tyr Gly Lys Glu Val Glu Phe Pro Ala Phe Val Asn Gly Trp Lys
            85                  90                  95

Glu Leu Ala Lys His Asp Leu Lys Leu Trp Ser Gln Asn Lys Lys Ser
            100                 105                 110

Leu Ile Arg Asn Trp Gly Glu Ala Val Phe Asp Ile Phe Asp Lys Asp
            115                 120                 125

Gly Ser Gly Ser Ile Ser Leu Asp Glu Trp Lys Thr Tyr Gly Gly Ile
            130                 135                 140

Ser Gly Ile Cys Pro Ser Asp Glu Asp Ala Glu Lys Thr Phe Lys His
145                 150                 155                 160

Cys Asp Leu Asp Asn Ser Gly Lys Leu Asp Val Asp Glu Met Thr Arg
                165                 170                 175

Gln His Leu Gly Phe Trp Tyr Thr Leu Asp Pro Asn Ala Asp Gly Leu
            180                 185             190

Tyr Gly Asn Phe Val Pro
        195
```